United States Patent
Whitaker et al.

(10) Patent No.: US 6,838,247 B2
(45) Date of Patent: Jan. 4, 2005

(54) TEST FOR LYME DISEASE

(75) Inventors: Jo Anne Whitaker, Tarpon Springs, FL (US); Eleanor G. Fort, Tarpon Springs, FL (US); Donna M. Hamilton, Holiday, FL (US)

(73) Assignee: Bowen Research and Training, Palm Harbor, FL (US)

( * ) Notice: Subject to any disclaimer, the term of this patent is extended or adjusted under 35 U.S.C. 154(b) by 96 days.

(21) Appl. No.: 10/174,664

(22) Filed: Jun. 19, 2002

(65) Prior Publication Data

US 2003/0235875 A1 Dec. 25, 2003

(51) Int. Cl.[7] .......................... G01N 33/53; C12Q 1/00; A61K 39/02

(52) U.S. Cl. ...................... 435/7.1; 424/9.1; 424/130.1; 424/150.1; 424/164.1; 424/184.1; 424/234.1; 435/4; 435/29; 436/501; 436/800

(58) Field of Search ............................... 424/9.1, 130.1, 424/150.1, 164.1, 184.1, 234.1; 435/4, 7.1, 29; 436/501, 800

*Primary Examiner*—Rodney P Swartz
(74) *Attorney, Agent, or Firm*—Dennis G. LaPointe; Mason Law, P.L.

(57) ABSTRACT

The present invention provides an accurate method to identify and quantify the *Borrelia burgdorferi* (Bb) antigen, the cause of Lyme Disease, in a sample of whole blood, body tissues and fluids of a subject, a human or animal subject. The qualitative method provides a quick, easy and accurate method of detection of the Bb antigen. The quantitative method allows for monitoring of treatment in conjunction with severity of clinical signs and symptoms.

10 Claims, No Drawings

TEST FOR LYME DISEASE

The invention relates to new methods for detecting the *Borrelia burgdorferi* (Bb) antigen, the causative agent of Lyme disease. These new methods provide physicians with an early, accurate and quick method for diagnosing Lyme disease and a quantitative method to aid in monitoring therapy.

Lyme disease is called the "New Great Imitator" because, like syphilis, it attacks multiple organ systems and mimics many diseases. Both diseases are caused by a spirochete. Lyme disease is caused by *Borrelia burgdorferi* (Bb), an elongated spiral shaped spirochete that infects humans and animals, carried by the deer tick (*Ixodes scapularis*). It is also transported by the common dog (wood) tick, deer flies, mosquitoes, birds and the white-footed mouse. Mattman and Whitaker's laboratories have found Bb in California and Florida mosquitoes. Lyme Disease, previously known as the most common tick-borne disease in the United States, now known to be carried by many "blood sucking" vectors, has become a serious global problem.

Lyme disease is a multi-system illness producing symptoms of fatigue, joint pain, muscle pain, as well as digestive, respiratory, endocrine, urinary, reproductive and nervous system problems. A critical review of the literature indicates that alterations in mood, memory and sleep are prominent features of this illness. Initial symptoms include acute headache, backache, chills, flu-like symptoms, fatigue and, some have a typical Erythema migrans (EM) rash at the biting site.

If ignored, the early symptoms may disappear, but more serious problems can develop months to years later. The later symptoms of Lyme disease can be quite severe and chronic. Fatigue, muscle and joint pain, arthritis of the large joints is common. Neurological symptoms include cognitive impairment, memory loss, depression, numbness, tingling and burning sensations in the extremities and Bell's palsy. Involvement of all systems such as heart, eye respiratory and gastrointestinal problems can develop. Premature births, stillbirths, birth defects and transplacental infection of the fetus have been reported. Symptoms are often intermittent lasting from a few days to several months and sometimes years. Chronic Lyme disease, because of its diverse symptoms, mimics many other diseases and can be difficult to diagnose.

Treatment

Successful management and treatment of Lyme disease rests on early and accurate diagnosis. Timely treatment increases chances of recovery and may lessen the severity of any later symptoms. The most effective treatment will depend on how soon antibiotics are started after the bite of a vector infected with Bb. Treatment for later stages is more difficult often requiring extended and repeated courses of antibiotic therapy. The diagnostic tests now being used for Lyme disease are neither sensitive nor specific and consequently results are not reliable.

It is well known that the serologic blood test for Lyme is insensitive, inaccurate and misses more than forty percent (40%) of cases. It is important to understand the nature of the Bb organism. Bb can change its shape from a spiral to a filament, cyst, granule, hooked rod or elbow. These variants are called L-forms, a name given by the Lister Institute where they were first studied. These L-forms are also called cell-wall deficient (CWD) bacteria taking the non-spiral shape when they have lost much of the cell wall. In this form, they do not produce an antibody response, as they have no cell wall surface components for the individual's immune systems to recognize as foreign. Classic L-forms are active metabolism centers for the production of CWD pleomorphic Bb organisms. In this form they are able to hide within most tissues in the body, thus protecting them from any host response adverse to their well-being. CWD organisms can revert to typical morphology and may revert into adult forms of other genera, depending on the milieu. For this reason most of the diagnostic tests like the ELISA and the Western Blot, which depend on the production of antibodies, are inadequate. Much like the hepatitis model, antigen is present early after initial infection. Later there is an antibody response in about 70% of patients. Tests that look for antibody response will not support an early diagnosis, nor reliably confirm presence of the disease.

The ELISA is the most commonly used screening test for the primary diagnosis of Lyme disease but if positive has to be confirmed by the Western Blot. This test is recommended at least four weeks after exposure and consequently is not helpful in making an early definitive diagnosis. Both the ELISA and the Western Blot are not quantitative and do not assess the severity of an infection.

The polymerase chain reaction (PCR) is a sensitive and valuable diagnostic laboratory test to validate many different diseases, however, in Lyme disease, due to low numbers of Bb organisms, it is frequently falsely negative. One possibility is that the *Borellia* genome contains many plasmids, which may vary their expression altering the proteins analyzed by a PCR analysis. This allows *Borellia* to evade PCR analysis the same way it evades our own bodies' immune system.

SUMMARY OF INVENTION

The present invention provides a qualitative and quantitative method of detecting the antigen of *Borrelia burgdorferi* (the causative agent of Lyme disease) in whole blood, fluid and/or tissue and a quantitative titration (serial dilution) method of detecting the number of fluorescing cellular structures in a series of dilutions of whole blood samples of a specimen. Fluorescein tagged Bb antibody is applied to whole blood creating an antibody-antigen reaction, and examined with suitable fluorescent detecting devices for evidence of fluorescing structures in infected cellular material. Fluorescent detecting devices are known in the art, including microscopy and scanner based devices.

The present invention provides a qualitative and quantitative method of detecting *Borrelia burgdorferi* antigen in whole blood, fluid and/or tissue. By quantitating a serial dilution and establishing a titration factor, one can demonstrate the increase or decrease of the titer. The titration factor along with severity of clinical signs and symptoms can be used as a tool to determine the effectiveness of treatments.

DETAILED DESCRIPTION OF THE INVENTION

The present invention provides a method of detecting *Borrelia burgdorferi* antigen in a whole blood or other body fluids or tissue samples of a subject comprising contacting the sample with fluorescein Labeled Affinity Purified *Borrelia burgdorferi* antibody, examining the sample with a fluorescent detecting device and detecting an antigen-antibody complex, whereby the detection of an antigen, which is demonstrated by the presence of a fluorescing infected cellular structure, detects the *Borrelia burgdorferi* antigen in the sample. As used throughout, by a "subject" is meant an individual. Thus, the "subject" can include domesticated animals, such as cats, dogs, etc., livestock (e.g., cattle, horses, pigs, sheep, goats, etc.), laboratory animals (e.g., mouse, rabbit, rat, guinea pig, etc.) and birds. Preferably, the subject is a mammal such as a primate, and, more preferably, a human.

*Borrelia burgdorferi* (Bb) can exist in several forms, for example, L-forms, spheroplasts, protoplasts, wall-deficient bacteria and wall-intact bacteria. It is sometimes difficult to detect by conventional microbiological stains and cultures. Most con entional stains used to detect bacteria are directed to the cell wall of the organism. Thus, when bacterium does not have a cell wall, its presence in a sample may not be detected when the only ethod used for detecting the bacterium is conventional staining.

Because of the inadequacy of the prior art to detect Bb, Lyme Disease has been under-diagnosed with resulting unnecessary morbidity for affected patients. Thus, there exists a great need to have a fast, simple diagnostic test to detect the bacterium in a fluid sample from a patient so that appropriate antibiotic therapy can be started as soon as possible to prevent the disease from becoming chronic. The present invention overcomes the previous limitations and shortcomings in the art by providing an easy, fast and accurate diagnostic test which can not only detect the presence of Bb in any of its physical forms but also determines the concentration of fluorescing cellular structures at specific titration's.

The present invention provides an accurate test because the antibody used is fluorescein labeled and specific for the Bb antigen. The antibody will form an antigen-antibody complex only in the presence of an antigen of Bb. Thus, the antibody of this invention binds its target antigen to form an antigen-antibody complex, which is detectable by fluorescence.

The fluorescein-Labeled Affinity Purified *Borrelia burgdorferi* antibody is commercially available from Kirkegaard & Perry Laboratories, Inc., 2 Cessna Court, Gaithersburg, Md. 20879 and Accurate Chemical & Scientific Corp., 30 Shames Drive, Westbury, N.Y. 11590.

Qualitative and Quantitative Method

The present invention further provides a method of detecting the *Borrelia burgdorferi* antigen, in whole blood, and body fluids and tissues. The whole blood specimen is collected in EDTA, using a transfer pipette, add 1.0 mls of whole blood and 4 mls of 0.85% NaCl and centrifuge at 1500 RPMs for 3 minutes. The supernate is removed by using a transfer pipette, being careful not to disturb the buffy-coat. The remaining buffy-coat and blood cells are mixed by tapping the bottom of the tube several times. 25 ul of this mixture is added to a clean labeled disposable glass culture tube along with 50 ul of fluorescein-labeled *Borrelia burgdorferi* antibody and centrifuged at 1500 RPMs for 15 seconds and mixed by gently rotating the culture tube and allow to incubate for 60 minutes at ambient temperature. Ten (10) ul of treated specimen is placed in a suitable container or on a slide and covered with a cover slip in preparation for examination under a fluorescent microscoper or other fluorescent detecting device. A whole blood sample prepared according to the methods of the present invention is a "direct fluorescent assay."

By examining a direct fluorescent assay, a person can continually observe a blood sample to look for an antibody/antigen reaction in the form of live fluorescing cellular structures. Examining a conventionally dried and fixed microscopic slide preparation only allows a skilled person of the art to look for dead bacteria, which cannot change into other forms or increase in number.

To detect the antigen-antibody complexes, a person can use a microscope with a fluorescence mercury ARC photo optic lamp (HBO) and dark-field condenser with 10× and 100× oil emersion objective to detect the Bb antigen. Phase microscopy is used to identify the nature of the green fluorescing structure. Other fluorescent detectors can be employed for this task.

Also provided by the present invention is a quantitative method of identifying *Borrelia burgdorferi* antigen, the causative agent of Lyme disease using a serial dilution (titration) method and a fluorescent antibody technique (FAT), which involves the interaction of an antigen-antibody reaction. Fluorescent Antibody Technique (FAT) is being used in conjunction with a serial dilution method as a new laboratory test for the detection of *Borrelia burgdorferi* antigen that quantitates the number of fluorescing infected cellular structures and when correlated with the severity of clinical symptoms, assessment of treatment can be evaluated. The quantitative test is a method to determine Concentration of fluorescing cellular structures by serial (doubled) dilutions (titration).

Specifically a person can add 0.5 ml of blood using a transfer pipette from a well-mixed EDTA collection tube of blood to a clean glass culture tube containing 4 ml of 0.85% sodium chloride, which is centrifuged at 1500 RPMs for 3 minutes. The supernate is removed by using a transfer pipette, being careful not to disturb the bully-coat, the remaining packed red blood cells are gently mixed by tapping the bottom of the tube several times. This specimen, "washed blood cells", is used to make the titration.

Label seven (7) tubes with subject identification number and dilution factor. Add 0.5 mls of 10% Phosphate buffered saline to each of the seven tubes. Add 0.5 ml. of "washed cells" to tube number 1, mix well by gently tapping bottom of tube. Add 0.5 ml. of dilution from tube #1 to tube #2 with an automatic pipette, mix well by aspirating and dispensing solution in and out of tube with pipette until solution is homogenous. Add 0.5 ml. of dilution from tube #2 to tube #3 with an automatic pipette, mix well by aspirating and dispensing in and out of tube with pipette until solution is homogenous. Add 0.5 ml. of dilution from tube #3 to tube #4 with an automatic pipette, mix well by aspirating and dispensing in and out of tube with pipette until solution is homogenous. Add 0.5 ml. of dilution from tube #4 to tube #5 with an automatic pipette, mix well by aspirating and dispensing in and out of tube with pipette until solution is homogenous. Add 0.5 ml. of dilution from tube #4 to tube #5 with an automatic pipette, mix well by aspirating and dispensing in and out of tube with pipette until solution is homogenous. Add 0.5 ml. of dilution from tube #5 to tube #6 with an automatic pipette, mix well by aspirating and dispensing in and out of tube with pipette until solution is homogenous. Add 0.5 ml. of dilution from tube #6 to tube #7 with an automatic pipette, mix well by aspirating and dispensing in and out of tube with pipette until solution is homogenous. Label seven (7) additional tubes with patient identification number and dilution factor. Using a 25 ul calibrated automatic pipette transfer 25 ul of 1:2 dilution to tube #1, transfer 25 ul of 1:4 dilution to tube #2, transfer 25 ul of 1:8 dilution to tube #3, transfer 25 ul of 1:16 dilution to tube #4, transfer 25 ul of 1:32 dilution to tube #5, transfer 25 ul of 1:64 dilution to tube #6, transfer 25 ul of 1:128 to tube #7. Save dilution tube #7 for further diluting if necessary. Centrifuge the 7 tubes for 15 seconds at 1500 RPMs and mix by gently tapping the culture tube. Allow culture tubes to incubate for 60 minutes at ambient temperature.

Ten (10) ul of mixed sample for each dilution is placed in a suitable container or on a slide and covered with a cover slide in preparation for examination under a microscope or other fluorescent detecting using the technique described above. The entire 10 ul sample is scanned for the presence of fluorescing structures. The last dilution of the series showing fluorescence is recorded as the titer ratio.

E-coli Negative Control

Label culture tube with patient identification and add 50 ul of Fluorescein Labeled antibody to *E. coli* 0157:H7 and 25 ul of washed packed blood cells. Centrifuge at 1500 RPMs for 15 seconds. Remove from centrifuge and mix by gently tapping bottom of tube, then allow tube to incubate at ambient temperature for at least 60 minutes. After incubation period make one (1) slide per specimen (labeled with information on tube) by placing 10 ul of mixed sample to slide and cover with cover slide and examine using a fluorescent microscope or other fluorescent detecting device. No fluorescence should be observed (negative control). A negative control is performed on every sample tested.

The present invention is more particularly described in the following examples, which are intended as illustrative only since numerous modifications and variations therein will be apparent to those skilled in the art.

Principle:

This is a qualitative and a quantitative serial dilution test to identify *Borrelia burgdorferi*, the causative agent of Lyme disease using a fluorescent antibody technique (FAT), which involves the interaction of an antigen-antibody reaction. The fluorescent antibody technique is a specific method for detecting many types of bacteria in fluid and/or tissue of an individual by using a fluorescein labeled antibody to detect the targeted bacteria. Fluorescent Antibody Technique (FAT) is being used in conjunction with a serial dilution method to develop a new laboratory test for the detection of *Borrelia burgdorferi* and quantitate the number of fluorescing cellular structures. The qualitative test is a 1:2 diluted specimen treated with Fluorescein-Labeled Affinity Purified Antibody to *Borrelia burgdorferi* (produced in Goat) and then examined by fluorescent microscopy or other fluorescent detecting devices. The quantitative test is a method to determine concentration of fluorescing cellular structures by serial (doubled) dilutions (titration).

Specimen:

Patient Preparation: No special patient preparation

Type of Specimen: Any body fluid, blood and/or tissue; whole blood is the specimen of choice.

Specimen Handling:

4. Tissue samples are submitted in a sterile container containing 0.85% Normal Saline.
5. Fluids are submitted in a sterile container with NO preservative.
6. Blood samples are submitted in EDTA vacutainer (lavender-topped) tube.

Typical Equipment:

10. A quality research grade microscope: Olympus BX-40 with mechanical stage, 10×, and 100×/1.25 Ph3 oil and 100× oil immersion with iris diaphragm objectives.
11. Light, dark field and phase 1, 2 and 3 condensers which can be rotated into the light path while observing the same microscopic field in order to best visualize all dimensions of the cells under scrutiny.
12. An ultraviolet halogen lamp (HBO) for viewing fluorescence or a suitable fluorescence detector.
13. Hitachi color video camera with digital signal and monitor (color system).
14. A computer with high-resolution monitor attached by a specially designed cable to the camera for direct photography of the microscopic field without distortion.
15. Tektronix phaser 750-color laser printer.
16. Software for storage and photograph preparation.
17. High quality paper for printing photographs.
18. Sero-Fuge centrifuge (1500 RPMs)

Supplies:

13. Glass slides 1 mm×25 mm×75 mm (Number 1)
14. Glass cover slips 22 mm×50 mm (Number 1 Thickness)
15. Disposable glass culture tubes size 12×75 mm.
16. Liquipette polyethylene transfer pipette 7.0 ml
17. Calibrated digital variable volume macropipettors, 0.2–2.0 ml
18. Macro-pipettor tips (2 ml)
19. Calibrated Air displacement variable volume pipettor 10–100 ul
20. Micro-pipettor tips (200 ul)
21. Sodium Chloride 0.85% (Normal Saline)
22. 10% Phosphate buffered saline (PBS)
23. Fluorescein-Labeled Affinity Purified Antibody to *Borrelia burgdorferi* antigen (produced in Goat)
24. Fluorescein-Labeled Affinity Purified Antibody to *E. coli* 0157:H7 (produced in Goat)

Quantitative (Serial Dilution) Method:

8. Label one 12×75 clean glass disposable culture tube with specimen accession number.
9. Add 4 ml of 0.85% sodium chloride to culture tube
10. Thoroughly mix specimen tube (whole blood collected in EDTA tube) by gently inverting tube 6 times.
11. Add 1.0 ml of well-mixed whole blood using an automatic transfer pipette.
12. Centrifuge at 1500 RPMs for 3 minutes.
13. Remove and discard supernatant using a transfer pipette, being careful not to disturb buffy-coat.
14. Gently mix the remaining packed red blood cells by tapping the bottom of the tube several times (the remaining specimen is washed blood cells and used to make the titration as described below).

| Titration (Serial Dilution) | | | | | | | |
|---|---|---|---|---|---|---|---|
| 1:2 DF | 1:4 DF | 1:8 DF | 1:16 DF | 1:32 DF | 1:64 DF | 1:128 DF | |
| Tube #1 | Tube #2 | Tube #3 | Tube #4 | Tube #5 | Tube #6 | Tube #7 | |
| 0.5 ml PBS | 0.5 ml PBS | 0.5 ml PBS | 0.5 ml PBS | 0.5 ml PBS | 0.5 ml PBS | 0.5 ml PBS | |
| 0.5 ml WPBC | 0.5 ml of T #1 | 0.5 ml of T #2 | 0.5 ml of T #3 | 0.5 ml of T #4 | 0.5 ml of T #5 | 0.5 ml of T #6 | Discard 0.5 ml of T #7 |

T—Tube
WPBC—Washed Packed Blood Cells PBS - 10% Phosphate Buffered Saline
DF—Dilution Factor 1. Label 7 tubes with specimen accession number and dilution factor (see chart above).
2. Add 0.5 mls of 10% Phosphate buffered saline to each of the seven tubes
3. Add 0.5 ml. of "washed packed red cells" to tube number 1, mix well by gently tapping bottom of tube.
4. Add 0.5 ml. of diluted specimen from tube #1 to tube #2 with an automatic pipette, mix well by aspirating and dispensing solution in and out of tube with pipette until solution is homogeneous.
5. Add 0.5 ml. of dilution from tube #2 to tube #3 with an automatic pipette, mix well by aspirating and dispensing solution in and out of tube with pipette until solution is homogeneous.
6. Add 0.5 ml. of dilution from tube #3 to tube #4 with an automatic pipette, mix well by aspirating and dispensing solution in and out of tube with pipette until solution is homogeneous.
7. Add 0.5 ml. of dilution from tube #4 to tube #5 with an automatic pipette, mix well by aspirating and dispensing solution in and out of tube with pipette until solution is homogeneous.
8. Add 0.5 ml. of dilution from tube #4 to tube #5 with an automatic pipette, mix well by aspirating and dispensing solution in and out of tube with pipette until solution is homogeneous.
9. Add 0.5 ml. of dilution from tube #5 to tube #6 with an automatic pipette, mix well by aspirating and dispensing solution in and out of tube with pipette until solution is homogeneous.
10. Add 0.5 ml. of dilution from tube #6 to tube #7 with an automatic pipette, mix well by aspirating and dispensing solution in and out of tube with pipette until solution is homogeneous.
11. Label 7 additional tubes with specimen accession number and dilution factor.
12. To each tube add 50 ul of Bb antibody with a calibrated automatic pipette.
13. Transfer 25 ul of 1:2 diluted specimen to tube #1, transfer 25 ul of 1:4 diluted specimen to tube #2, transfer 25 ul of 1:8 diluted specimen to tube #3, transfer 25 ul of 1:16 diluted specimen to tube #4, transfer 25 ul of 1:32 diluted specimen to tube #5, transfer 25 ul of 1:64 diluted specimen to tube #6, transfer 25 ul of 1:128 diluted specimen to tube #7, using a 25 ul calibrated automatic pipette for each transfer. Save dilution tube #7 for further diluting if necessary.
14. Centrifuge the 7 tubes for 15 seconds and mix by gently rotating tube.
15. Gently mix solution.
16. Allow tubes to incubate for 60 minutes at room temperature.
17. Label 25×1×75 mm slides with specimen accession number and dilution factor, and place 10 ul of well-mixed sample to slide and apply 22×50 mm cover slip.
18. Examine slide using a fluorescent detecting device.
19. Record results as last dilution factor where fluorescing cellular structures are found.

Qualitative Method

1. Label a 12×75 glass disposable culture tube with specimen accession number.
2. Add 4 ml of 0.85% sodium chloride to tube.
3. Gently invert EDTA tube 6 times, ensuring thorough mixing of specimen.
4. Add 1.0 ml of well-mixed (EDTA) whole blood using a transfer pipette
5. Centrifuge at 1500 RPMs for 3 minutes.
6. Remove and discard supernatant using a transfer pipette, being careful not to disturb buffy-coat.
7. Gently mix the washed packed red cells by tapping bottom of tube several times.
8. Label a 12×75 culture tube with specimen accession number.
9. Place 500 uls of washed packed blood cells in tube, add 500 uls of PBS buffer and mix gently.
10. To labeled tube, add 50 ul of fluorescein-labeled *Borrelia burgdorferi* antibody and 25 ul of well-mixed washed packed red cells.
11. Centrifuge tube at 1500 RPMs for 15 seconds and mix by gentle rotation of tube.
12. Allow tube to incubate for 60 minutes at ambient temperature.
13. Label glass slides and place 10 ul of mixed specimen to slide and apply cover slip.
14. Examine slide using a fluorescent detecting device for cellular structures.

*E-Coli* Negative Control

1. Label 12×75 culture tube with specimen accession number and E.C. (*E. coli* negative control)
2. Add 50 ul of Fluorescein Labeled antibody to *E. coli* 0157:H7 and 25 ul of specimen washed packed 1:2 blood cells.
3. Centrifuge for 15 seconds. Remove from centrifuge and mix by gently rotating bottom of tube. Allow tube to incubate at ambient temperature for a 60 minutes.
4. After incubation period, place 10 ul of mixed sample to a labeled slide and cover with cover slide or place in a suitable container for other forms of fluorescent detection.
5. Examine slide using a fluorescent detecting device for fluorescing structures.
6. No fluorescing structures should be observed (negative control).
7. Perform negative control on each sample tested.

What is claimed is:

1. An improvement in the method for detecting *Borrelia burgdorferi* in a fluid or tissue sample of a human or mammal by direct analysis of the sample, the improved method comprising:

a) contacting the sample with an antibody labeled with a fluorescent dye, the antibody being specific for *Borrelia burgdorferi;* b) examining the sample of step a) with a fluorescent detecting device; and c) using a specific direct analysis for the quantitaion and identification of the *Borrelia burgdorferi*, detecting a fluorescent structure, wherein the detection of the fluorescent structure demonstrates the presence of the *Borrelia burgdorferi* in the sample.

2. The method of claim 1, wherein the antigen is in a form selected from the group consisting of L-forms, spheroplasts, protoplasts, wall-deficient bacterium, wall-intact bacterium, cysts and cellular structures containing pleomorphic forms.

3. The method of claim 1, wherein the fluid sample is selected from the group consisting of whole blood, including buffy-coat, and all body fluids.

4. An improvement in the method of diagnosing Lyme Disease bacterium in a human or animal subject by direct analysis of a fluid or tissue sample from the subject, the improved method comprising:

a) contacting a fluid or tissue sample from the subject with an antibody labeled with a fluorescent dye, the antibody being specific for *Borrelia burgdorferi* (Bb);

b) examining the sample of step a) with a fluorescent detecting device; and c) using a specific direct analysis for the quantitaion and identification of the *Borrelia burgdorferi*, detecting a fluorescent structure, wherein the detection of the fluorescent structure demonstrates the presence of the *Borrelia burgdorferi*, the causative agent of Lyme disease in the subject.

5. The method of claim 4, wherein the bacterium is in a form selected from the group consisting of L-forms, spheroplasts, protoplasts, wall-deficient bacterium, wall-intact bacterium, cysts and cellular structures containing pleomorphic forms.

6. The method of claim 4, wherein the fluid sample is selected from the group consisting of whole blood, including buffy-coat, and all body fluids.

7. An improvement in a method of quantitatively detecting and identifying the *Borrelia burgdorferi* (Bb) by a specific direct analysis of fluid samples from a human subject, *Borrelia burgdorferi* (Bb) being the causative agent for Lyme disease in said human subject, the improved method comprising:

a) creating a series of fluid samples from the subject, each of the series being of a different dilution;

b) contacting each of the series with an antibody labeled with a fluorescent dye, the antibody being a specific for *Borrelia burgdorferi* (Bb);

c) examining each of the series of samples with a fluorescent detecting device; and d) detecting the number of fluorescing cellular structures.

8. The method of claim 7, wherein the series is formed by serial dilution.

9. The method of claim 7, wherein the antigen is in a form selected from the group consisting of L-forms, spheroplasts, protoplasts, wall-deficient bacterium, wall-intact bacterium, cysts and cellular structures containing pleomorphic forms.

10. The method of claim 7, wherein the fluid sample is selected from the group consisting of whole blood, including buffy-coat.

\* \* \* \* \*